US009655590B2

United States Patent
Yu (10) Patent No.: US 9,655,590 B2
(45) Date of Patent: May 23, 2017

(54) APPARATUS, SYSTEM AND METHOD FOR MULTI-MODAL VOLUMETRIC ULTRASOUND IMAGING AND BIOPSY OF A SINGLE BREAST

(71) Applicant: XCISION MEDICAL SYSTEMS, LLC, Columbia, MD (US)

(72) Inventor: Xinsheng Cedric Yu, Pasadena, MD (US)

( * ) Notice: Subject to any disclaimer, the term of this patent is extended or adjusted under 35 U.S.C. 154(b) by 591 days.

(21) Appl. No.: 14/179,497

(22) Filed: Feb. 12, 2014

(65) Prior Publication Data

US 2014/0235962 A1 Aug. 21, 2014

Related U.S. Application Data

(60) Provisional application No. 61/765,793, filed on Feb. 17, 2013.

(51) Int. Cl.
| | |
|---|---|
| *A61B 8/00* | (2006.01) |
| *A61B 8/08* | (2006.01) |
| *A61B 10/02* | (2006.01) |
| *A61B 8/15* | (2006.01) |
| *A61B 8/14* | (2006.01) |
| *A61B 17/32* | (2006.01) |
| *A61B 90/17* | (2016.01) |
| *A61N 7/02* | (2006.01) |

(Continued)

(52) U.S. Cl.
CPC ............ *A61B 8/403* (2013.01); *A61B 8/0825* (2013.01); *A61B 8/0841* (2013.01); *A61B 8/145* (2013.01); *A61B 8/15* (2013.01); *A61B 8/4209* (2013.01); *A61B 8/4227* (2013.01); *A61B 8/4281* (2013.01); *A61B 8/4494* (2013.01); *A61B 8/5207* (2013.01); *A61B 10/0233* (2013.01); *A61B 17/320068* (2013.01); *A61B 90/17* (2016.02); *A61N 5/1049* (2013.01); *A61N 7/00* (2013.01); *A61N 5/103* (2013.01); *A61N 7/02* (2013.01); *A61N 2005/1058* (2013.01); *A61N 2007/0052* (2013.01)

(58) Field of Classification Search
None
See application file for complete search history.

(56) References Cited

U.S. PATENT DOCUMENTS

| | | | |
|---|---|---|---|
| 7,850,613 B2 | 12/2010 | Stribling | |
| 2012/0022376 A1* | 1/2012 | Amara | A61B 8/0825 600/443 |

(Continued)

OTHER PUBLICATIONS

Dines et al., "Ultrasonic Attenuation Tomography of Soft Tissues," *Ultrasonic Imaging*, 1(1): 16-33 (1979).

(Continued)

*Primary Examiner* — Jonathan Cwern
(74) *Attorney, Agent, or Firm* — Carol Larcher; Larcher & Chao Law Group (57) ABSTRACT

An apparatus for volumetric ultrasound imaging of a breast using different modes, including transmission, reflection and the speed of sound, which apparatus comprises a negatively pressurized breast imaging cup with integrated ultrasound transducers and an ultrasound coupling mechanism; an ultrasound system comprising the apparatus; and a method of imaging a breast in three dimensions without moving the ultrasound transducers.

26 Claims, 4 Drawing Sheets

(51) Int. Cl.
*A61N 7/00* (2006.01)
*A61N 5/10* (2006.01)

(56) References Cited

U.S. PATENT DOCUMENTS

2012/0245463 A1* 9/2012 Mertelmeier .......... A61B 6/025
  600/427
2013/0267850 A1* 10/2013 Berman ............... A61B 8/0825
  600/443

OTHER PUBLICATIONS

Duric et al., "Detection of breast cancer with ultrasound tomography: First results with the Computed Ultrasound Risk Evaluation (CURE) prototype," *Med. Phys.*, 34(2):773-785 (2007).
Duric et al, "Development of ultrasound tomography for breast imaging: Technical assessment," 32(5): *Med. Phys.*, 1375-1386 (2005).
Nebeker et al., "Imaging of Sound Speed Using Reflection Ultrasound Tomography," *J. Ultrasound Med.*, 31: 1389-1404 (2012).
Norton et al., "Ultrasonic Reflectivity Tomography: Reconstruction with Circular Transducer Arrays," *Ultrasonic Imaging*, 1: 154-184 (1979).

\* cited by examiner

FIG. 1

Multi-Modality Single Breast imager

APPARATUS, SYSTEM AND METHOD FOR MULTI-MODAL VOLUMETRIC ULTRASOUND IMAGING AND BIOPSY OF A SINGLE BREAST

CROSS REFERENCE TO RELATED APPLICATIONS

This application claims priority to U.S. provisional patent application No. 61/765,793, which was filed on Feb. 17, 2013, and which is hereby incorporated by reference in its entirety.

TECHNICAL FIELD

The present invention generally relates to medical imaging and, more particularly, a method, an apparatus, and a system for imaging a breast, specifically a method, an apparatus, and a system for imaging a breast using ultrasound waves.

BACKGROUND

Breast cancer is the most prevalent malignancy among women. More than 200,000 cases of breast cancer were diagnosed in the United States in 2010 (Cancer Facts & Figures, 2011, American Cancer Society). The lifetime risk of getting breast cancer for any particular patient in North America is about 1 in 7.

On a more promising note, breast cancer awareness and screening have allowed most breast cancer cases to be diagnosed at an early-stage. Most clinicians agree that early detection of breast cancer saves thousands of lives each year. Screenings are important as breast cancer does not cause obvious symptoms until the cancer has grown and possibly spread beyond the breast, significantly lowering the treatment success rate. At an early stage, however, breast cancer is smaller and still confined within the breast, thereby enabling an easier and more effective treatment. The current standard of treatment for most early-stage breast cancers is breast conservation therapy (BCT), consisting of lumpectomy followed by 6-8 weeks of radiation therapy.

The predominant method used for breast cancer screening is mammography. A mammogram is an x-ray projection of the breast, usually producing two images of each breast. The American College of Radiology (ACR) and the American Medical Association (AMA) recommend that women aged 40 years and over have a mammogram every year in order to ensure detection of breast cancer at an early stage.

Mammography, however, has several drawbacks that limit its detection ability and efficiency. Due to the two-dimensional nature of mammography, it is sometimes difficult to see a tumor that is obscured by dense tissue, such as the breast tissue of younger or pregnant women. Underlying and overlying breast tissue also can hide a tumor from view. In addition, the procedure for a mammogram requires the breast to be uncomfortably compressed between two plastic plates in order to produce a readable image. The use of x-rays, itself, is potentially harmful as patients receive a small amount of radiation during the mammogram, and ionizing radiation is known to increase cancer risk.

Digital tomosynthesis (DTS) is a pseudo 3-D x-ray imaging modality that has been extensively investigated for diagnostic imaging and image guidance in radiotherapy (Dobbins et al., Phys. Med. Biol. 48(19): R65-R106 (2003); Niklason et al., Radiology 205(2): 399-406 (1997); Suryanarayanan et al., Acad. Radiol. 7(12): 1085-1097 (2000); Wu et al., Med. Phys. 30(3): 365-380 (2003); and Wu et al., Int. J. Radiat. Oncol., Biol., Phys. 69(2): 598-606 (2007)). Like mammography, the procedure for DTS requires the breast to be compressed between two plastic plates while being imaged. Additionally, DTS requires more ionizing radiation to be used, since many projection images at different beam angles are necessary, and the resulting tomographic-like images are slices, which are parallel and close to the in-focus plane and moderate in quality.

It has been reported that magnetic resonance imaging (MRI) is more sensitive than mammography in identifying certain types of breast cancer (Kriege et al., N. Engl. J. Med. 351: 427-437 (2004); Lehman et al., J. Surg. Oncol. 92: 9-15 (2005a); Lehman et al., Cancer 103: 1898-1905 (2005b); and Leach et al., Lancet 365: 1769-1778 (2005)). Numerous clinical trials have demonstrated that MRI more accurately defines the true extent and type of breast disease than mammography alone or a mammography-ultrasound combination (Lehman et al. (2005a), supra; Lehman et al. (2005b), supra; Kuhl et al., J. Clin. Oncol. 23: 8469-8476 (2005)). However, due to the long imaging time and the associated high cost, MRI is only approved for screening high-risk patients. The false positive rate of MRI is also very high, leading to more unnecessary biopsies.

Ultrasound imaging is regularly used to supplement mammography in breast cancer screening because it provides high-resolution images with great soft tissue contrast compared with mammography. Given that it is non-invasive and does not involve the use of ionizing radiation, ultrasound is a widely used modality in medical imaging.

Existing ultrasound imaging methods, which can be used for clinical breast imaging, are designed to image a breast in the conventional reflection mode (B-mode). Such methods are commonly used to supplement mammograms because ultrasound can more easily differentiate between benign and cancerous masses. However, the dependence of conventional ultrasound on an operator has been a major obstacle for extensive use.

In the 1970s and 1980s researchers showed that it is also possible to construct breast images by measuring the transmission and refraction of ultrasound waves through the breast and calculating the speed of the ultrasound propagation at different locations in the breast (Greenleaf et al., in *Acoustical Holography*, edited by P. S. Green, Plenum, New York, volume 6, pages 71-90 (1975); Carson et al., Science 214: 1141-1143 (1981); Devaney, IEEE Trans. Biomed. Eng. BME-30: 377-386 (1983); and Devaney, Ultrason. Imaging 4: 336-350 (1982)). These multi-modal ultrasound techniques offer the promise of operator-independent, tomographic imaging of breast lesions. Proposed tomographic ultrasound imaging systems for single breast imaging have utilized these multiple ultrasound imaging modes.

Reflection imaging measures margins, or spans, of different masses in the breast. The images generated by reflection indicate changes on the surface of breast tissues. By analyzing these parameters in addition to the pulse-echo properties of ultrasound, accurate differentiation of benign and cancerous masses can be achieved. However, accurate differentiation with reflection imaging is operator-dependent and does not measure the transmission parameters, sound speed, and attenuation of the ultrasound wave in the breast.

Transmission imaging has shown itself to be an effective method of breast cancer screening that is operator-independent. In a study by Greenleaf et al. in 1977 (Ultrasonics Symposium: 989-995) in vitro samples were used to measure the sound speed and attenuation of different types of breast tissue. This study found that on a plot of sound speed vs. attenuation, malignant breast masses and benign masses have distinct sound speeds and attenuations. These findings indicate breast tissues of any density have sound speeds and attenuations that are very different from the sound speed and attenuation of cancerous masses. This makes transmission imaging a very valuable tool in differentiating between dense breast tissue and malignant breast lesions, which is hard to discern with mammography.

Whiting and Koch (U.S. Pat. No. 4,509,368) laid the ground work for tomographic ultrasound breast imaging. They disclosed a mechanism submersed in a water bath for scanning a single breast pendent in the water bath. It was envisioned that reflection, transmission, and sound speed could be used for tomographic reconstruction of the breast. Over the past 30 years, the work of others in the area has been described in numerous publications. For example, Shehada (U.S. Pat. No. 7,264,592 B2) discloses a tomographic ultrasound imaging apparatus for imaging a single breast that is submerged in a water tank.

Recently, Techniscan, Inc., constructed a functional multimodal ultrasound tomography system similar to that of Whiting and Koch. A clinical trial using the system for breast cancer screening has been conducted and shown great promise for imaging breast lesions. Techniscan uses two transducer arrays that revolve around the breast, one of which fires the transmission ultrasound waves, to collect data on both the transmitted and reflected waves. Using the collected data, they use inverse scattering techniques to reconstruct a 3-D image of the breast.

Another example of multimodal ultrasound breast imaging is the Computed Ultrasound Risk Evaluation system (C.U.R.E.) developed by Delphinus Technologies. C.U.R.E. uses a ring transducer, which eliminates the need to rotate the transducer array and also accounts for scatter in all directions along the image plane. In one imaging cycle of the C.U.R.E., all of the transducers take a turn firing an ultrasound signal, while the rest listen for the sound peak to arrive. Then, the ring translates downwards and repeats the process until the entire breast has been imaged. The use of reflection and transmission imaging while detecting 360 degrees of scatter makes this system capable of producing images with much higher resolution and greater specificity than mammography.

However, these systems have drawbacks that hinder their prevalence. For example, they use a water bath to submerge the entire breast, which can be messy and indecent to the patient. In addition, due to the size of the water tank, the patient must climb a ladder to get onto the imaging bed. Because these systems are large and somewhat inconvenient, they have not gained widespread clinical use.

In view of the above, there remains a need for a method, an apparatus, and a system of imaging a breast that does not suffer from the disadvantages attendant the use of the methods and the systems currently available in the art. An object of the present invention is to provide such a method, an apparatus, and a system. This and other objects and advantages, as well as inventive features, will become apparent from the detailed description provided herein.

SUMMARY

An apparatus for immobilizing and ultrasound imaging of a breast is provided. The apparatus comprises a breast imaging cup, which has an open end and which comprises (a) an inner breast cup assembly, which comprises (i) a continuous, concave and pliable inner breast cup for placement of a breast to be imaged, and (ii) an annular flange at the open end of the inner breast cup, and (b) an outer breast cup assembly, which comprises (i) a continuous, concave and rigid outer breast cup comprising a plurality of channels and a plurality of biopsy ports, (ii) a plurality of ultrasound transducers, and (iii) a plurality of pushing stems, each of which has an inner end and an outer end, wherein an ultrasound transducer is mounted on the inner end of a pushing stem, and the pushing stem-mounted ultrasound transducer is air-tightly fitted in a separate channel in the outer breast cup, and the pushing stem can move along the channel. The outer breast cup assembly is removably attached to the annular flange of the inner breast cup assembly. The outer breast cup assembly is optionally encased.

An ultrasound system for imaging a breast is also provided. The system comprises an apparatus for immobilizing and ultrasound imaging of a breast, an ultrasound control, and a computer for image reconstruction and display.

Further provided is a method of imaging a breast with ultrasound. The method comprises (a) placing the breast in an apparatus for immobilizing and ultrasound imaging of a breast, (b) using a source of vacuum to apply negative pressure to the breast and scanning the breast with ultrasound until each of the plurality of ultrasound transducers successively transmits an ultrasound pulse while the remainder of the plurality of ultrasound transducers detects the transmission of the ultrasound pulse, a reflection of the transmitted ultrasound pulse, and a time-of-flight thereof, and (c) reconstructing images of the breast comprising an image based on the detection of the transmissions of the ultrasound pulses, an image based on the reflections of the transmitted ultrasound pulses, and an image based on the times-of-flight. The apparatus is part of an ultrasound system.

Still further provided is a method of irradiating a target in a breast that has been imaged with the volumetric ultrasound imaging system. The method comprises (a) releasing negative pressure applied to the breast during imaging; (b) removing the outer breast cup assembly from the patient while leaving the inner breast cup assembly attached to the patient; (c) attaching a treatment cup to the inner breast cup assembly in the same manner as the outer breast cup assembly was attached to the inner breast cup assembly during imaging without altering the attachment of the inner breast cup assembly to the patient; (d) reapplying the same negative pressure as that applied to the breast during imaging; (e) placing the patient, whose breast is in the treatment cup, on a patient support of a radiation treatment system, and securing the treatment cup to the patient support; and, (f) based on a target delineated on the volumetric ultrasound images obtained using the volumetric ultrasound imaging system, directing radiation at the target in the breast.

Even still further provided is a method of ablating a target in a breast that has been imaged with the volumetric ultrasound imaging system. The method comprises (a) releasing negative pressure applied to the breast during imaging; (b) removing the outer breast cup assembly from the patient while leaving the inner breast cup assembly attached to the patient; (c) attaching a treatment cup to the inner breast cup assembly in the same manner as the outer breast cup assembly was attached to the inner breast cup assembly without altering the attachment of the inner breast cup assembly to the patient; (d) reapplying the same negative pressure as that applied to the breast during imaging; (e) connecting the treatment cup, to a high-intensity, focused ultrasound treatment system; and, (f) based on a target delineated on volumetric ultrasound images obtained using the volumetric ultrasound imaging system, directing high-intensity, focused ultrasound at the target in the breast.

BRIEF DESCRIPTION OF THE FIGURES

FIG. 4 depicts the system architecture. It includes a control unit, which generates an ultrasound signal and receives ultrasound signals and linear displacement inputs, and a volumetric 3-D image reconstruction and display system.

DETAILED DESCRIPTION

The present disclosure seeks to provide an apparatus, a system and a method for volumetric ultrasound imaging of a breast. The apparatus, the system, and the method do not suffer from the disadvantages attendant the use of the systems and the methods currently available in the art, such as patient set-up and the need for a water bath. Instead of a water bath, the system employs a breast imaging cup, such as a multi-layered or bi-layered breast cup, e.g., a breast imaging cup comprising an outer breast cup and an inner breast cup, and vacuum suction. The arrangement of ultrasound transducers employed in the context of the present disclosure differs from the circular geometry, i.e., ring or ring-like arrangement of ultrasound transducers, or circular scanning around the breast employed in the art. Rather than being arranged in a ring, the ultrasound transducers are arranged all over the breast, thereby allowing transmission from one transducer to all other transducers, such as in succession, and consequently enabling reconstruction of volumetric images of the breast without any physical movement or scanning of the transducers. The system also can be used to guide biopsy and ultrasound or radiation treatment of breast cancer.

The following terms are used herein:

(a) "breast imaging cup" may be used to refer to an inner breast cup assembly attached to an outer breast cup assembly, wherein the outer breast cup assembly is optionally covered with a further outer breast cup, which encases the outer surface of the outer breast cup assembly.

(b) "inner breast cup" may be used to refer to the inner breast cup of a breast imaging cup. The inner breast cup is continuous, concave, and pliable. Preferably, and even desirably, the inner breast cup is stretchable. Even more preferably, and even more desirably, the inner breast cup is stretchable and perforated.

(c) "inner breast cup assembly" may be used to refer to an inner breast cup and an annular flange. The inner breast cup and the annular flange can be unitary in construction; alternatively, the inner breast cup and the annular flange can be fabricated separately and attached to each other, such as in accordance with methods described herein.

(d) "outer breast cup" may be used to refer to the outer breast cup of a breast imaging cup. The outer breast cup is continuous, concave, and rigid. The outer breast cup comprises channels and biopsy ports.

(e) "outer breast cup assembly" may be used to refer to an outer breast cup with a plurality of ultrasound transducers air-tightly fitted into channels (i.e., with pushing stems, optional spring pushers, which can be loaded, and linear encoders) in the outer breast cup. "Outer breast cup assembly" also may be used to refer to an outer breast cup with a plurality of ultrasound transducers air-tightly fitted into channels in the outer breast cup and at least one biopsy port, such as a plurality of biopsy ports, in the outer breast cup. The outer breast cup assembly can comprise a further outer breast cup, which encases the outer surface of the outer breast cup assembly.

The above terminology is provided for the purpose of describing particular embodiments. The terminology is not intended to be limiting.

In view of the above, an apparatus for immobilizing and ultrasound imaging of a breast is provided. The apparatus comprises a breast imaging cup, which has an open end and which comprises (a) an inner breast cup assembly, which comprises (i) a continuous, concave and pliable inner breast cup for placement of a breast to be imaged and (ii) an annular flange at the open end of the inner breast cup and (b) an outer breast cup assembly, which comprises (i) a continuous, concave and rigid outer breast cup comprising a plurality of channels and a plurality of biopsy ports, (ii) a plurality of ultrasound transducers, and (iii) a plurality of pushing stems, each of which has an inner end and an outer end, wherein an ultrasound transducer is mounted on the inner end of a pushing stem, and the pushing stem-mounted ultrasound transducer is air-tightly fitted in a separate channel in the outer breast cup, and the pushing stem can move along the channel. The outer breast cup assembly is removably attached to the annular flange of the inner breast cup assembly. The outer breast cup assembly is optionally encased.

The inner breast cup can be made of any suitable pliable material, which preferably is stretchable. More preferably, the inner breast cup is also perforated so that a vacuum can be applied to assist in fitting the inner breast cup to a human breast. In this regard, the inner breast cup can provide a custom fit for a given breast. Examples of pliable materials that can be used for the inner breast cup include, but are not limited to, silicone, latex, and polyurethane (e.g., viscoelastic polyurethane or low resilience polyurethane). In this regard, a higher-density material preferably softens in response to body heat, thereby allowing it to mold to a breast, whereas a lower-density material preferably conforms to the shape of a breast when the breast exerts pressure on the inner surface of the inner breast cup. The overall three-dimensional size of the inner breast cup can vary to accommodate different sizes of breasts, such as a size of breast corresponding to a cup size of a bra or sizes of breasts corresponding to a range of cup sizes of bras. In this regard, the use of an outer breast cup, which has a diameter that is larger, even substantially larger, than the diameter of the inner breast cup provides space to accommodate differently sized breasts and allows an outer breast cup of a given diameter to be used with inner breast cups of varying size.

The annular flange can be an integral part of the inner breast cup (i.e., unitary construction) or separate from and attachable to the inner breast cup. If the flange is separate from and attachable to the inner breast cup, any suitable means can be used to attach the inner breast cup to the flange. The inner layer of the breast cup can be attached to the flange, for example, by using a plastic zipper, such as on a re-sealable plastic bag, and the like. Preferably, the inner breast cup and the flange are single-use components of the apparatus. The outer breast cup also can be, and desirably is, attached to the annular flange by any suitable means. The annular flange preferably is soft and preferably adheres safely and removably to the chest wall of a patient whose breast is to be imaged. In this regard, the flange can be made of any suitable pliable material, such as silicone, the surface (such as the inner surface, which faces the chest wall) of which is inherently adherent or treated/coated to render it adherent. Preferably, the flange enables the inner breast cup to be fitted to the patient and the entire breast imaging cup assembly to achieve an air-tight fitting to the patient's chest wall.

The outer breast cup can be made of any suitable material, such as plastic (e.g., polycarbonate, polypropylene), which can be molded, such as by extrusion molding or injection molding, and maintains its shape. The breast cup desirably has sufficient rigidity to withstand the level of a vacuum, when applied to the breast imaging cup to assist in fitting of the breast imaging cup to a human breast, and the weight of a leaning body, the breast of which is being imaged. Preferably, and even desirably, the outer breast cup is of uniform thickness, such as in the range of about 2 mm to about 10 mm. The overall three-dimensional size of the outer layer of the breast cup can vary to accommodate different sizes of breasts and chest wall curvatures. Desirably, there are numerous inner breast cups (e.g., 3, 4, 5, 6, 7, 8, 9, 10 or more) for each outer breast cup to accommodate all sizes of breasts.

The outer breast cup comprises channels. The channels preferably are distributed throughout the outer breast cup, such as throughout most, substantially all, or all the outer breast cup. While the channels can have any suitable shape, preferably the channels are cylindrical. Also, while the channels can pass through the outer breast cup in various orientations, preferably the channels pass through the outer breast cup perpendicularly to the outer surface of the outer breast cup. The channels can be uniformly distributed or can vary in density from one area to another. The diameters of the channels should be sufficient to accommodate an ultrasound transducer. Within each channel, a rubber "O" ring can be, and preferably is, fitted closely to each end of the channel, such that the pushing stem with smooth surface and an ultrasound transducer mounted at the inner end can be air-tightly fitted and can move through the channel to make contact with the outer surface of the inner cup.

The pushing stem can have any suitable shape. Preferably, the pushing stem is cylindrical, particularly when the channel, through which the pushing stem-mounted ultrasound transducer is inserted, is cylindrical. The pushing stem can move along a channel to allow a deeper insertion or a shallower insertion into the outer breast cup. More than one ultrasound transducer can be mounted on the end of each pushing stem. In a preferred embodiment a two-dimensional array of ultrasound transducers is mounted at the end of each pushing stem.

Preferably, the outer breast cup assembly comprises a plurality of spring pushers, which can be loaded. Each spring pusher is attached to the outer end of a pushing stem and maintains contact between the ultrasound transducer and the outer surface of the inner breast cup. When each transducer or array of transducers is mounted on a pushing stem that protrudes through the outer breast cup, a spring pusher is also preferably, and even desirably, applied to the transducer stem such that, if there is no resistance from inside the outer breast cup, the spring pusher keeps the transducer at its deepest insertion.

For the purpose of volumetric image reconstruction, the level of insertion (or level of displacement) of the pushing stem is detected. Preferably, the outer breast cup assembly comprises a plurality of linear encoders, wherein each linear encoder is attached to a pushing stem and detects the level of displacement of the pushing stem. Typically, the length of transducer stem insertion is longer at positions closer to the nipple side of the cup than those closer to the chest wall of the patient whose breast is being imaged.

The apparatus can further comprise a vacuum inlet passing through the outer breast cup. The vacuum inlet can pass through the outer breast cup in a region of the outer breast cup that is adjacent to a nipple of a breast placed in the breast imaging cup. Preferably and even desirably, negative pressure is applied to ensure a tight fit between the breast to be imaged and the breast imaging cup, alone or in further combination with the flange. In this regard, the outer breast cup is preferably, even desirably, air-tight, and the inner breast cup is deformable, e.g., through the application of negative pressure. In this regard, perforation of the inner breast cup can assist in achieving a gapless fit between the skin of the breast, which is coated with ultrasound coupling gel, and the inner surface of the inner breast cup. The application of negative pressure secures the breast imaging cup to the patient, and pulls the breast tissue into the inner breast cup, which stretches to accommodate the additional breast tissue, and purges any air pocket in the inner breast cup so that the breast skin is tightly against the inner surface of the inner breast cup. The vacuum between the inner breast cup and the outer breast cup helps pull the pushing stem in through the channel in the outer breast cup towards the outer surface of the inner breast cup so that the transducers, which are also coated with ultrasound coupling gel, maintain constant contact with the outer surface of the inner breast cup, which preferably is also a good sound conductor. The application of negative pressure also serves to pull the breast tissue away from and perpendicular to the chest wall so that all breast tissues are imaged.

The outer breast cup also comprises at least one biopsy port. The biopsy port can be a "soft spot," such as a solid rubber or rubber-like plastic material or a channel, such as a self-sealing channel, which can be sealed by radial squeezing at insertion. A biopsy needle can be inserted in a biopsy port (e.g., a soft sport or a channel) and through the inner breast cup and into the breast to obtain a tissue sample from the breast being imaged. A biopsy port can be selected to minimize the depth of tissue to be traversed by the biopsy needle to reach the lesion in the breast to be biopsied. The biopsy ports preferably are interspersed with the channels and distributed throughout the outer breast cup, such as throughout most, substantially all, or all the outer breast cup. The biopsy ports can have any suitable shape, such as cylindrical, similar to the inflation valve of a ball (e.g., basketball). While the biopsy ports can pass through the outer breast cup in various orientations, preferably the biopsy ports pass through the outer breast cup perpendicularly to the outer surface of the outer breast cup. The biopsy ports can be uniformly distributed or can vary in density from one area to another. The diameters of the biopsy ports should be sufficient to accommodate a biopsy needle. The material and construction of the biopsy port should preserve the negative pressure without significant air leaks when a biopsy needle is inserted, such that the breast geometry is maintained. "Biopsy ports" can be introduced, such as irreversibly introduced (e.g., inserted), either after the rigid outer breast cup is molded or during the molding process.

The breast imaging cup is assembled by attaching the outer breast cup assembly to the inner breast cup assembly. For example, the outer breast cup assembly can be slid over an O-ring-like coupling at the junction of the inner breast cup and the annular flange to form an air-tight seal. The breast imaging cup can be connected to a stereotactic biopsy apparatus. The arc-shaped frame of the stereotactic biopsy apparatus can rotate relative to the base, and the needle guide can slide along the arc, always pointing at the isocenter. The arc's base can make a lateral translation (r-movement) and a vertical movement (z-movement). Preferably, and even desirably, each biopsy port allows some degree of angulation relative to the direction perpendicular to the outer surface of the outer breast cup. If a suspicious region is revealed in the images, a needle biopsy can be performed at the time of breast imaging using the stereotactic biopsy apparatus and a biopsy planning system, which determines the r- and z-shifts, the two rotation angles, and the depth of the needle advancement parameters for the biopsy apparatus, without altering the geometry of the imaging, such as by breaking a vacuum used to fit the breast to the breast imaging cup. Preferably, the imaging computer is able to determine the best port to use, the needle angle, and the depth of insertion.

The breast imaging cup also can be attached to a treatment system, such as a high-intensity, focused ultrasound treatment system or radiation treatment system. By removing the negative pressure applied through the vacuum port, the outer breast cup assembly can be separated from the inner breast cup assembly. While keeping the inner breast cup assembly on the patient, an alternative cup or device can be attached to the inner breast cup assembly, and negative pressure can be re-established to reproduce the imaging geometry of the breast. Therefore, a cancerous lesion identified during volumetric ultrasound imaging can be accurately targeted for treatment. A high-intensity, focused ultrasound treatment system destroys cancerous cells through cavitations and heating. A radiation treatment system can deliver an effective dose of radiation to the cancerous lesion identified in the breast.

Figure 1:
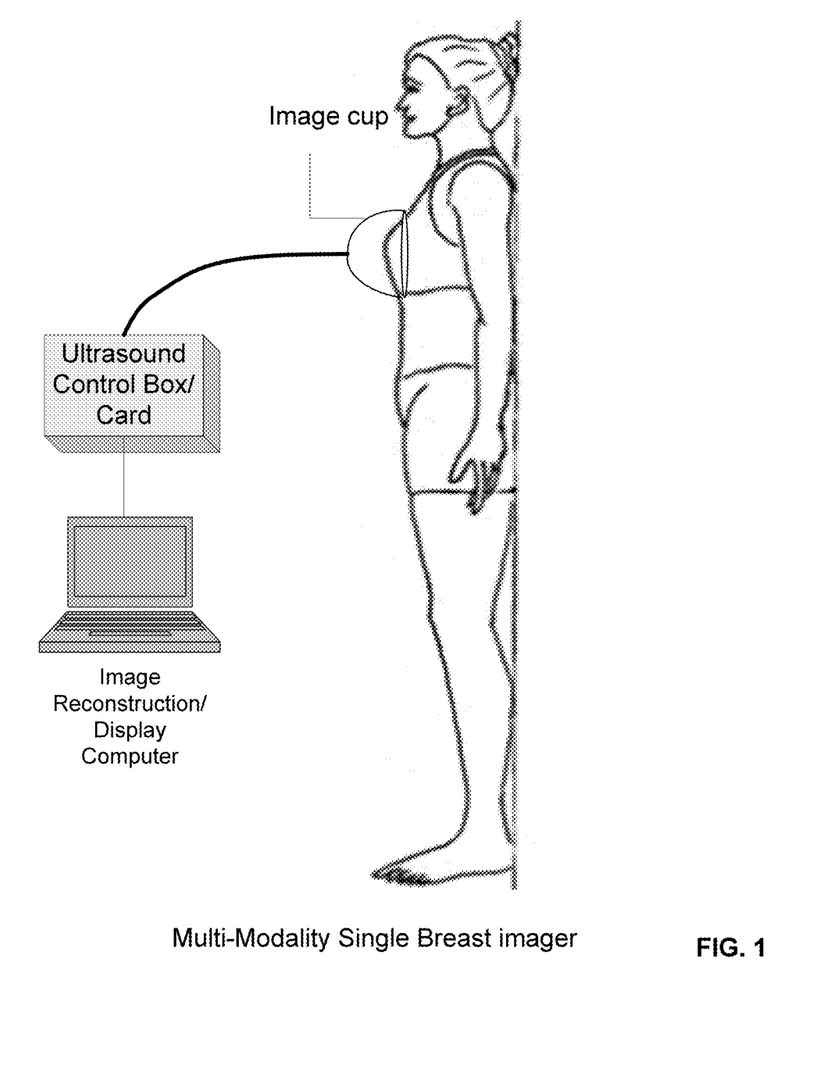
FIG. 1 is a schematic diagram of the single breast volumetric ultrasound imaging system used for breast cancer screening, in which the breast of a patient in a standing position is being imaged with a breast imaging cup connected by a cable to an ultrasound control, which contains the ultrasound pulsing and sensing unit and which, in turn, is connected to a computer for image reconstruction and display.
Figure 2:
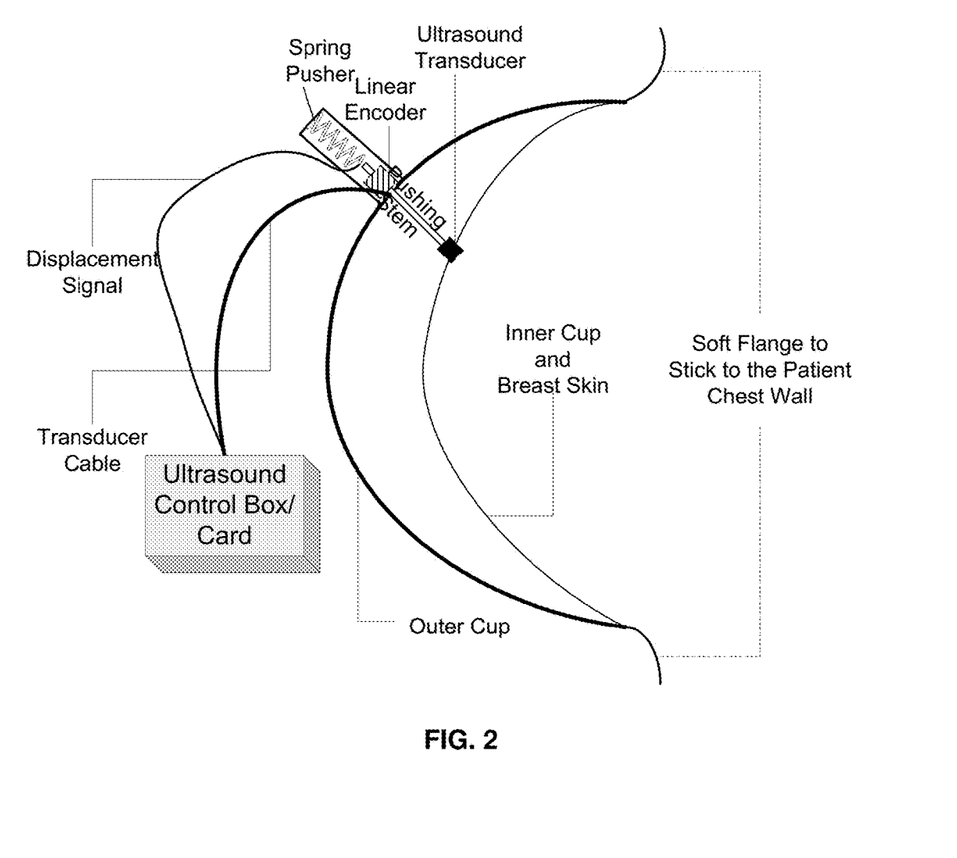
FIG. 2 depicts a single ultrasound transducer, which can be part of an array of ultrasound transducers. The stem of the ultrasound transducer is inserted through the outer breast cup to the outer surface of the inner breast cup. Also shown is a soft flange, which adheres to the chest wall of the patient whose breast is to be imaged, a spring pusher that pushes the ultrasound transducer stem to the innermost position (i.e., the outer surface of the inner breast cup), a transducer cable connecting the transducer to an ultrasound control, and a linear encoder, which transmits the level of insertion (displacement signal) of the transducer stem to the ultrasound control.
Figure 3:
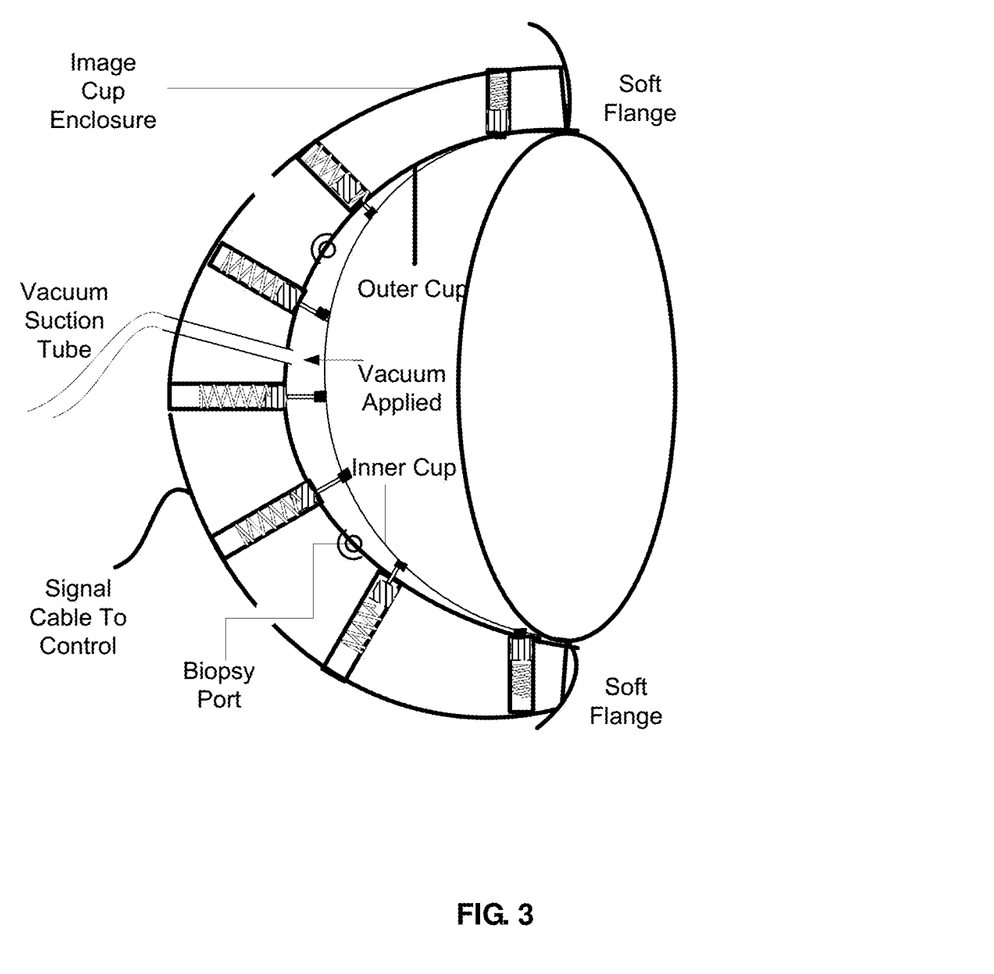
FIG. 3 depicts multiple ultrasound transducers, the stems of which are inserted through the outer breast cup to the outer surface of the inner breast cup. In this embodiment the pushing stems, to which are attached the multiple ultrasound transducers, along with the spring pushers and linear encoders, are inserted air-tightly in the channels distributed in the outer breast cup and are enclosed. Also shown is a vacuum suction tube for application of negative pressure to the space between the outer breast cup and the inner breast cup, a signal cable, two biopsy ports, and a soft flange, which adheres to the chest wall of the patient whose breast is to be imaged. In this embodiment a single signal cable (e.g., with hundreds or thousands of wires in it) can be used to connect the breast imaging cup and the ultrasound control.
Figure 4:
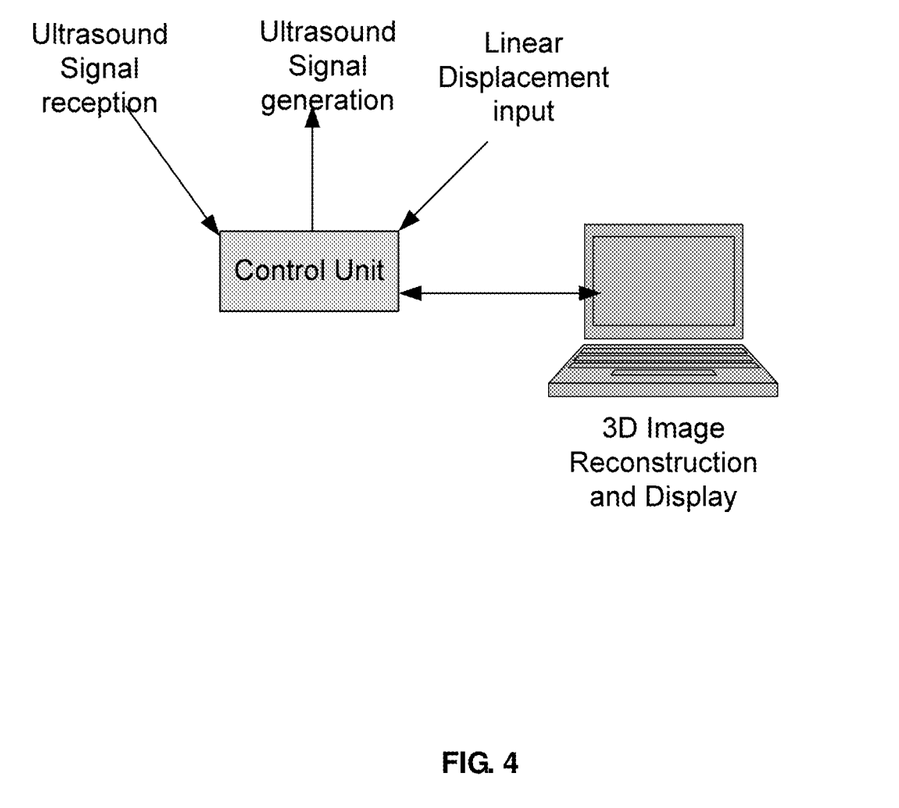

In a preferred embodiment the outer breast cup assembly is encased (see, e.g., FIG. 3). In this embodiment, a single cable can be used to connect the breast imaging cup to an ultrasound control unit.

In view of the above, also provided is an ultrasound system for imaging a breast. The system comprises an above-described apparatus, an ultrasound control, and a computer for image reconstruction and display. All of the ultrasound transducers are connected to the ultrasound control. Each of the plurality of ultrasound transducers can successively transmit an ultrasound pulse while the remainder of the plurality of ultrasound transducers detects the transmission of the ultrasound pulse, a reflection of the transmitted ultrasound pulse, and a time-of-flight thereof. The path of the ultrasound pulse between the ultrasound transducer, which transmits the ultrasound pulse, and those ultrasound transducers, which detect the transmission, the reflection, and the time-of-flight of the ultrasound pulse, is non-coplanar. Preferably, and even desirably, the attenuation, the reflection, and the speed of sound are calculated for each signal detected at a location in the breast using an iterative algorithm. Three-dimensional images of different modes can then be constructed. The apparatus can comprise biopsy planning software that ascertains the optimal biopsy port and the angle and the depth of insertion of a biopsy needle. By removing the negative pressure applied through the vacuum port, the outer breast cup assembly can be separated from the inner breast cup assembly at the flange to allow the inner breast cup assembly to be attached to a treatment system, such as a high-intensity, focused ultrasound treatment system or a radiation treatment system, such as via a treatment cup (e.g., a thin, rigid treatment cup) that can be attached to a patient support system, while maintaining a three-dimensional coordinate system shared by the ultrasound imaging and treatment systems. Negative pressure can be re-established to reproduce the imaging geometry of the breast. Thus, the system can further comprise ultrasound/radiation treatment planning software.

The ultrasound system can be portable, such as when the apparatus comprising the breast imaging cup replaces the probe in a traditional ultrasound unit. Alternatively, the ultrasound system can be stationary, like a mammography unit.

In view of the above, a method of imaging a breast with ultrasound is provided. The method comprises placing the breast in an apparatus for immobilizing and ultrasound imaging of a breast as described above, wherein the apparatus is part of an ultrasound system. The method further comprises using a source of vacuum in fluid communication with the vacuum inlet to apply negative pressure to the breast, and scanning the breast with ultrasound until each of the plurality of ultrasound transducers successively transmits an ultrasound pulse while the remainder of the plurality of ultrasound transducers detects the transmission of the ultrasound pulse, a reflection of the transmitted ultrasound pulse, and a time-of-flight thereof, and reconstructing images of the breast comprising an image based on the detection of the transmissions of the ultrasound pulses, an image based on the reflections of the transmitted ultrasound pulses, and an image based on the times-of-flight.

A patient, whose breast is to be imaged, first places her breast, which is coated with ultrasound gel, in an inner breast cup assembly comprising a correctly sized inner breast cup and an annular flange, which is either an integral part of the inner breast cup or attached thereto. If the flange and the inner breast cup are separate, preferably, and even desirably, the flange and the inner breast cup are self-sealing or attachable, such as by adhesive (e.g., liquid, spray, or tape), circular plastic snap-lock strips (like on re-sealable plastic bags), and the like. The flange preferably safely and removably adheres to the patient's chest wall. The annular flange is then attached to the chest wall all around the breast to be imaged. Any suitable means can be used to attach the flange to the chest wall, such as tape. If necessary or desired, a chest strap and/or shoulder strap can be used to maintain the position of the inner breast cup assembly on the patient. The patient then can position her breast, which is already in the inner breast cup assembly, in the outer breast cup assembly, and a secure and air-tight connection can be established. In this regard, different ways of coupling the inner breast cup assembly to the outer breast cup assembly are possible. For example, the outer breast cup assembly can slide onto the annular flange, such as when the annular flange comprises an O ring or O ring-like feature. The ultrasound transducers are attached to an ultrasound control unit via a signal cable.

Preferably, and even desirably, the outer layer, with all of the transducers already attached, mates with the annular flange, such as via a mechanical locking or interlocking mechanism in a predetermined geometric arrangement, to form a secure and air-tight connection. An air-tight connection allows the application of a vacuum (i.e., mild negative pressure) between the inner breast cup and outer breast cup, thereby pulling the breast tissues into the inner breast cup and causing the inner breast cup to expand. The presence of perforations in the inner breast cup ensures that no air bubbles form between the inner breast cup and the skin of the breast so that the ultrasound is transmitted to and through the breast. The application of vacuum also immobilizes the breast substantially perpendicular to the anterior plane of the body to reduce motion during imaging and ensures that the transducer is in constant contact with, and gently pressed against, the outer surface of the inner breast cup. The imaging breast cup allows the entire breast to be imaged by a multimodal ultrasound imager when the patient is in a standing position. If necessary or desired, the imaging system can be adapted for imaging the breast while the patient is in a seated position.

A strap may be used to secure the patient to the imaging unit. However, because the imaging time is very short, more extensive immobilization is unnecessary. An under-arm support can be used for older patients, who are more likely to slouch during the procedure.

The method can further comprise identifying a suspicious lesion in the breast and obtaining a needle biopsy of the suspicious lesion, such as by insertion of a biopsy needle through a selected biopsy port in the outer breast cup without releasing the negative pressure and disturbing the imaging geometry. If a suspicious lesion is identified, the method can further comprise determining that the suspicious lesion in the breast is cancerous and treating the cancerous lesion, such as with high-intensity focused ultrasound or radiation. Alternatively, the method can further comprise locating a previously identified cancerous lesion in the breast and treating the cancerous lesion, such as with high-intensity, focused ultrasound or radiation.

Thus, the breast imaging cup enables operator-independent placement of multiple ultrasound transducers around and in contact with the breast, and, consequently, image quality is operator-independent. The entire breast up to the chest wall can be imaged. In this regard, the use of spring-loaded transducer stems ensures that contact between the transducers and the outer surface of the inner breast cup is maintained during imaging. In addition, the cup immobilizes the breast during imaging, while eliminating the need for a water bath, which is traditionally associated with breast ultrasound tomographic methods. The positioning of multiple transducers on and through the outer breast cup in a spatial arrangement that covers the entire breast allows each receiver to measure signals from multiple non-coplanar pulses at the same time, thereby allowing the use of more sophisticated algorithms, which, in turn, allows better reconstruction of tomographic images, and minimal imaging time. Such an improvement in image reconstruction and a reduction in imaging time (also due to absence of mechanical moving parts) are not possible with currently available methods that employ a rotating detector pair or a single ring of detectors for imaging, which need to be moved from one position to another during imaging. In addition, the presence of at least one needle biopsy port, such as at least two biopsy ports, at least three biopsy ports, or more biopsy ports, enables real-time, image-guided needle biopsy, which is not possible with water-bath volumetric ultrasound imaging. Furthermore, because only part of the chest wall is against the imager while most of the circumference of the torso is free, breathing should have little effect on image quality. Also, because only multiple ultrasound transducers and corresponding data channels are required for imaging, the hardware costs of such a system will not be higher than a digital mammography system, yet the system provides better soft tissue contrast and, consequently, better sensitivity and specificity in determining the presence of breast cancer. Since the system does not require the use of mechanical moving parts, the system is more reliable.

The volumetric ultrasound imaging system can be integrated with a radiation treatment system or a high-intensity focused ultrasound treatment system so that radiation therapy or ultrasound therapy, respectively, can be image-guided. Preferably, a patient undergoing treatment with such an integrated system is in a supine or a prone position on a patient support, e.g., a couch. The patient can wear the same inner breast cup assembly, which desirably interchangeably attaches to an outer breast cup assembly and a treatment cup, which preferably, and even desirably, is thin, rigid, and does not comprise ultrasound transducers but which has the same coupling mechanism as that of the outer breast cup assembly. The same negative pressure can be applied as for ultrasound imaging, thereby reproducing the imaging geometry. The relative position of the target can, therefore, be accurately transferred from the imaging device to the treatment device (e.g., high-intensity focused ultrasound device or radiation device). In a preferred embodiment the patient is imaged and later treated in the same prone (or supine) position. The ultrasound images are transferred to a treatment planning system, which enables a physician to delineate the target to be irradiated or ablated. The treatment planning system then can deliver an effective dose to the target while maximally sparing the surrounding normal breast tissue.

Thus, in view of the above, a method of irradiating a target in a breast that has been imaged with an above-described volumetric ultrasound imaging system is provided. The method comprises (a) releasing negative pressure applied to the breast during imaging, (b) removing the outer breast cup assembly from the patient while leaving the inner breast cup assembly attached to the patient, (c) attaching a treatment cup to the inner breast cup assembly in the same manner as the outer breast cup assembly was attached to the inner breast cup assembly during imaging without altering the attachment of the inner breast cup assembly to the patient, (d) reapplying the same negative pressure as that applied to the breast during imaging, (e) placing the patient, whose breast is in the treatment cup, on a patient support of a radiation treatment system, and securing the treatment cup to the patient support, and (f) based on a target delineated on volumetric ultrasound images obtained using the volumetric ultrasound imaging system, directing radiation at the target in the breast.

Also in view of the above, a method of ablating a target in a breast that has been imaged with an above-described volumetric ultrasound imaging system is provided. The method comprises (a) releasing negative pressure applied to the breast during imaging, (b) removing the outer breast cup assembly from the patient while leaving the inner breast cup assembly attached to the patient, (c) attaching a treatment cup to the inner breast cup assembly in the same manner as the outer breast cup assembly was attached to the inner breast cup assembly without altering the attachment of the inner breast cup assembly to the patient, (d) reapplying the same negative pressure as that applied to the breast during imaging, (e) connecting the treatment cup, to a high-intensity, focused ultrasound treatment system, and (f) based on a target delineated on volumetric ultrasound images obtained using the volumetric ultrasound imaging system, directing high-intensity, focused ultrasound at the target in the breast.

All patents, patent application publications, journal articles, textbooks, and other publications mentioned in the specification are indicative of the level of skill of those in the art to which the invention pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" include one or more methods and/or steps of the type described herein and/or apparent to those ordinarily skilled in the art upon reading the disclosure.

The terms and expressions, which have been employed, are used as terms of description and not of limitation. In this regard, where certain terms are defined and otherwise described or discussed elsewhere herein, all such definitions, descriptions, and discussions are intended to be attributed to such terms. There also is no intention in the use of such terms and expressions of excluding any equivalents of the features shown and described or portions thereof.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

What is claimed is:

1. An apparatus for immobilizing and ultrasound imaging of a breast comprising a breast imaging cup, which has an open end and which comprises:
   (a) an inner breast cup assembly, which comprises:
      (i) a continuous, concave and pliable inner breast cup for placement of a breast to be imaged, and
      (ii) an annular flange at the open end of the inner breast cup, and
   (b) an outer breast cup assembly, which comprises:
      (i) a continuous, concave and rigid outer breast cup comprising a plurality of channels and a plurality of biopsy ports,
      (ii) a plurality of pushing stems, each of which has an inner end and an outer end, and
      (iii) a plurality of ultrasound transducers, each of which is mounted on the inner end of a pushing stem of the plurality of pushing stems of (ii),
      wherein each of the pushing stems of the plurality of pushing stems of (ii), onto the inner end of which is mounted an ultrasound transducer of the plurality of ultrasound transducers of (iii), is in a separate airtight channel in the outer breast cup and can move along the channel, and
      wherein the outer breast cup assembly is removably attached to the annular flange of the inner breast cup assembly.

2. The apparatus of claim 1, which further comprises a vacuum inlet passing through the outer breast cup.

3. The apparatus of claim 2, wherein the vacuum inlet passes through a region of the outer breast cup opposite the open end.

4. The apparatus of claim 2, wherein the inner breast cup is perforated and stretchable.

5. The apparatus of claim 1, wherein the outer breast cup assembly further comprises (i) a plurality of spring pushers, wherein each spring pusher is attached to the outer end of a pushing stem and maintains contact between the ultrasound transducer and the outer surface of the inner breast cup, and (ii) a plurality of linear encoders, wherein each linear encoder is attached to a pushing stem, the outer end of which is attached to a spring pusher, and detects the level of displacement of the pushing stem.

6. The apparatus of claim 1, wherein the outer breast cup assembly is encased.

7. The apparatus of claim 1, wherein more than one ultrasound transducer of the plurality of ultrasound transducers of (b) (iii) is mounted on the inner end of a pushing stem of the plurality of pushing stems of (b) (ii).

8. The apparatus of claim 7, wherein, when more than one ultrasound transducer of the plurality of ultrasound transducers of b) (iii) is mounted on the inner end of a pushing stem of the plurality of pushing stems of (b) (ii), the ultrasound transducers form a two-dimensional array.

9. A method of imaging a breast with ultrasound, which method comprises:
   (a) placing the breast in an apparatus for immobilizing and ultrasound imaging of a breast, which apparatus is part of an ultrasound system comprising the apparatus, an ultrasound control, and a computer for image reconstruction and display, wherein the apparatus comprises:
      an inner breast cup assembly, which comprises:
         (i) a continuous, concave and pliable inner breast cup for placement of a breast to be imaged, and
         (ii) an annular flange at the open end of the inner breast cup, and
      an outer breast cup assembly, which comprises:
         (i) a continuous, concave and rigid outer breast cup comprising a plurality of channels, a plurality of biopsy ports, and a vacuum inlet,
         (ii) a plurality of pushing stems, each of which has an inner end and an outer end, and
         (iii) a plurality of ultrasound transducers, each of which is mounted on the inner end of a pushing stem of the plurality of pushing stems of (ii),
         wherein each of the pushing stems of the plurality of pushing stems of (ii), onto the inner end of which is mounted an ultrasound transducer of the plurality of ultrasound transducers of (iii), is in a separate air-tight channel in the outer breast cup, and wherein the outer breast cup assembly is removably attached to the annular flange of the inner breast cup assembly;

(b) using a source of vacuum in fluid communication with the vacuum inlet to apply negative pressure to the breast and scanning the breast with ultrasound until each of the plurality of ultrasound transducers successively transmits an ultrasound pulse while the remainder of the plurality of ultrasound transducers detects the transmission of the ultrasound pulse, a reflection of the transmitted ultrasound pulse, and a time-of-flight thereof; and (c) reconstructing images of the breast, which images comprise an image based on the detection of the transmissions of the ultrasound pulses, an image based on the reflections of the transmitted ultrasound pulses, and an image based on the times-of-flight, whereupon performing the method comprising (a), (b) and (c), a breast is imaged with ultrasound.

10. The method of claim 9, which further comprises after (a), (b), and (c):
(d) identifying a suspicious lesion in the breast, and
(e) obtaining a needle biopsy of the suspicious lesion by inserting a biopsy needle through a biopsy port without releasing the negative pressure applied to the breast for imaging, thereby maintaining the placement of the breast in the apparatus.

11. The method of claim 10, which further comprises:
(f) determining that the suspicious lesion in the breast is cancerous, and
(g) treating the cancerous lesion with radiation or high-intensity, focused ultrasound.

12. The method of claim 9, which further comprises after (a), (b), and (c):
(d) locating a previously identified cancerous lesion in the breast, and
(e) treating the cancerous lesion with radiation or high-intensity, focused ultrasound.

13. The method of claim 9, wherein multiple non-coplanar ultrasound pulses are detected and attenuation, reflection, and speed of sound are calculated for multiple non-coplanar ultrasound pulses detected at a location in the breast using an iterative algorithm.

14. The method of claim 9, wherein the outer breast cup assembly is encased.

15. The method of claim 9, wherein more than one ultrasound transducer of the plurality of ultrasound transducers of (b) (iii) is mounted on the inner end of a pushing stem of the plurality of pushing stems of (b) (ii).

16. The method of claim 15, wherein, when more than one ultrasound transducer of the plurality of ultrasound transducers of b) (iii) is mounted on the inner end of a pushing stem of the plurality of pushing stems of (b) (ii), the ultrasound transducers form a two-dimensional array.

17. An ultrasound system for imaging a breast comprising the apparatus of claim 1, an ultrasound control, and a computer for image reconstruction and display.

18. The ultrasound system of claim 17, wherein the apparatus further comprises a vacuum inlet passing through the outer breast cup and a source of vacuum in fluid communication with the vacuum inlet.

19. The ultrasound system of claim 18, wherein the vacuum inlet passes through a region of the outer breast cup opposite the open end.

20. The ultrasound system of claim 17, wherein the inner breast cup of the apparatus is perforated and stretchable.

21. The ultrasound system of claim 17, wherein the outer breast cup assembly further comprises (i) a plurality of spring pushers, wherein each spring pusher is attached to the outer end of a pushing stem and maintains contact between the ultrasound transducer and the outer surface of the inner breast cup, and (ii) a plurality of linear encoders, wherein each linear encoder is attached to a pushing stem, the outer end of which is attached to a spring pusher, and detects the level of displacement of the pushing stem.

22. The ultrasound system of claim 17, wherein the computer comprises biopsy planning software that ascertains the optimal biopsy port for insertion of the biopsy needle and the angle and the depth of insertion of the biopsy needle.

23. The ultrasound system of claim 17, which further comprises a treatment cup, which can be removably attached to the inner breast cup assembly and which can be attached to a high-intensity, focused ultrasound treatment system or a radiation treatment system.

24. The ultrasound system of claim 23, wherein the computer comprises treatment planning software.

25. A method of irradiating a target in a breast that has been imaged with the ultrasound system of claim 13, which method comprises:
(a) releasing negative pressure applied to the breast during imaging,
(b) removing the outer breast cup assembly from the patient while leaving the inner breast cup assembly attached to the patient,
(c) attaching a treatment cup to the inner breast cup assembly without altering the attachment of the inner breast cup assembly to the patient,
(d) reapplying the same amount of negative pressure as that which was applied to the breast during imaging,
(e) placing the patient, whose breast is in the treatment cup, on a patient support of a radiation treatment system, and securing the treatment cup to the patient support, and
(f) based on a target delineated on the images obtained using the ultrasound system, directing radiation at the target in the breast,
whereupon performing the method comprising (a), (b), (c), (d), (e), and (f) a target in a breast is accurately irradiated.

26. A method of ablating a target in a breast that has been imaged with the ultrasound system of claim 18, which method comprises:
(a) releasing negative pressure applied to the breast during imaging,
(b) removing the outer breast cup assembly from the patient while leaving the inner breast cup assembly attached to the patient,
(c) attaching a treatment cup to the inner breast cup assembly without altering the attachment of the inner breast cup assembly to the patient,
(d) reapplying the same amount of negative pressure as that which was applied to the breast during imaging,
(e) connecting the treatment cup, to a high-intensity, focused ultrasound treatment system, and
(f) based on a target delineated on images obtained using the ultrasound system, directing high-intensity, focused ultrasound at the target in the breast, whereupon performing the method comprising (a), (b), (c), (d), (e), and (f) a target in a breast is accurately ablated.

\* \* \* \* \*

UNITED STATES PATENT AND TRADEMARK OFFICE
CERTIFICATE OF CORRECTION

| | |
|---|---|
| PATENT NO. | : 9,655,590 B2 |
| APPLICATION NO. | : 14/179497 |
| DATED | : May 23, 2017 |
| INVENTOR(S) | : Xinsheng Cedric Yu |

It is certified that error appears in the above-identified patent and that said Letters Patent is hereby corrected as shown below:

In the Claims

In Column 16, Line 26, Claim 25 should depend from Claim 18.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*